US010857094B2

(12) United States Patent
Weiss

(10) Patent No.: US 10,857,094 B2
(45) Date of Patent: Dec. 8, 2020

(54) LUBRICATING AND MOISTURIZING COMPOSITION FOR HUMAN USE

(71) Applicant: Eric A. Weiss, Ponte Vedra Beach, FL (US)

(72) Inventor: Eric A. Weiss, Ponte Vedra Beach, FL (US)

( * ) Notice: Subject to any disclaimer, the term of this patent is extended or adjusted under 35 U.S.C. 154(b) by 289 days.

(21) Appl. No.: 15/252,437

(22) Filed: Aug. 31, 2016

(65) Prior Publication Data

US 2017/0056321 A1 Mar. 2, 2017

Related U.S. Application Data

(60) Provisional application No. 62/213,214, filed on Sep. 2, 2015.

(51) Int. Cl.

| | |
|---|---|
| ***A61K 36/889*** | (2006.01) |
| ***A61K 36/00*** | (2006.01) |
| ***A61K 9/00*** | (2006.01) |
| ***A61K 8/92*** | (2006.01) |
| ***A61K 36/185*** | (2006.01) |
| ***A61K 36/87*** | (2006.01) |
| ***A61K 9/06*** | (2006.01) |
| ***A61Q 19/00*** | (2006.01) |
| ***A61Q 17/00*** | (2006.01) |

(52) U.S. Cl.

CPC ............ *A61K 9/0034* (2013.01); *A61K 8/922* (2013.01); *A61K 9/06* (2013.01); *A61K 36/185* (2013.01); *A61K 36/87* (2013.01); *A61K 36/889* (2013.01); *A61Q 17/005* (2013.01); *A61Q 19/00* (2013.01)

(58) Field of Classification Search

None

See application file for complete search history.

(56) References Cited

U.S. PATENT DOCUMENTS

| | | | | |
|---|---|---|---|---|
| 7,060,306 | B2 | 6/2006 | Springstead | |
| 7,670,606 | B2 * | 3/2010 | Volkmann | A61K 36/064 424/184.1 |
| 8,491,940 | B2 | 7/2013 | Emington et al. | |
| 8,784,906 | B2 * | 7/2014 | Gaynor-Krupnick | A61K 36/28 424/725 |
| 9,061,049 | B2 | 6/2015 | Davies | |
| 2003/0170325 | A1 * | 9/2003 | Mermelstein | A61K 36/16 424/729 |
| 2013/0108599 | A1 * | 5/2013 | Comeaux | A61K 36/82 424/93.45 |
| 2015/0306063 | A1 * | 10/2015 | McGinnis | A61K 31/325 514/489 |
| 2016/0113869 | A1 * | 4/2016 | Farron | A61K 9/02 |
| 2016/0158134 | A1 * | 6/2016 | Disalvo | A61K 8/31 424/59 |

* cited by examiner

*Primary Examiner* — Michael Barker
*Assistant Examiner* — Randall O Winston
(74) *Attorney, Agent, or Firm* — Thomas C. Saitta

(57) ABSTRACT

A non-aqueous, anti-microbial, anti-fungal, low pH, lubricating and moisturizing composition adapted for topical or intra-vaginal use during sexual intercourse, the composition consisting essentially of approximately 55-70 vol. % shea butter, approximately 25-40 vol. % coconut oil and approximately 1-5 vol. % grapeseed oil. The composition may further contain no more than approximately 2 vol. % of a scenting component. The composition possesses a low pH to counter the pH elevating effects of semen, soap, menopause and menstruation.

14 Claims, No Drawings

LUBRICATING AND MOISTURIZING COMPOSITION FOR HUMAN USE

This application claims the benefit of U.S. Provisional Patent Application Ser. No. 62/213,214, filed Sep. 2, 2015.

BACKGROUND OF THE INVENTION

This application relates generally to the field of skin treatments, lotions, creams, bars, oils and topical compositions suitable for human use. More particularly, the invention relates to lubricating and moisturizing compositions suitable for topical and/or intra-vaginal use primarily during sexual activity.

Skin lubricants directed primarily at making sexual activity more comfortable and enjoyable are well known. Various lubricant compositions provide liquids, creams, lotions or solids for application to the body prior and during sexual activity. In addition to the requirement that the formulations be suitable for the intended use, such compositions should possess various other desirable qualities and characteristics, which include the use of organic materials as opposed to synthetic chemical components, suitability for use during foreplay as well as during intercourse, and suitability for use intra-vaginally and topically. It is further desirable for the compositions to be a moisturizer in addition to being a lubricant, to possess anti-fungal and anti-microbial properties, and to avoid the need for preservatives. It is further desirable for the compositions to possess a pH lower than the natural vaginal pH of 3.5-4.5 in order to counter the pH raising effects of semen, soap, menopause and menstruation, all of which increase the risk of vaginal infections. Most current intra-vaginal and topical lubricants are liquids, making them difficult and messy to apply. Almost all known lubricants are water-based or silicone-based, such that they do not possess the moisturizing and other desirable characteristics set out above.

It is an object of this invention to provide a triglyceride-based lubricating and moisturizing composition suitable for topical application to the human body and for intra-vaginal application, especially during sexual activity. It is a further object to provide such a composition that also possesses the desirable characteristics set out above, including the use of only natural organic components, the presence of anti-fungal and anti-microbial properties, and requiring no preservatives for storage. It is a further object to provide such a composition that possesses a pH lower than the natural vaginal pH of 3.5-4.5 in order to counter the pH raising effects of semen, soap, menopause and menstruation, all of which increase the risk of vaginal infections. It is a further object to provide such a composition that is a soft solid at room temperature yet liquefies at body temperature.

SUMMARY OF THE INVENTION

The invention is a lubricating and moisturizing composition or formulation for human use, the composition being especially suitable for use during foreplay and sexual intercourse and the composition being applicable topically or intra-vaginally. The composition consists essentially of three primary natural, organic ingredients or components—shea butter, coconut oil and grapeseed oil. The composition may also contain a scenting component, but this component is not essential nor does it enhance the lubricating and moisturizing properties of the composition.

In the preferred embodiment, the composition consists essentially of approximately 55-70 vol. % shea butter, approximately 25-40 vol. % coconut oil, and approximately 1-5 vol. % grapeseed oil. If present, the scenting component, such as for example lavender, jasmine, sandalwood, patchouli, sweet orange or ylang-ylang, alone or in combination, is preferably present at no more than approximately 2 vol. %. It is most preferred that no additional components, other than a scenting component, be added to the shea butter, coconut oil and grapeseed oil combination.

The composition is a soft, high viscosity solid at room temperature but liquefies at body temperature, making application relatively easy, possesses anti-fungal and anti-bacterial/microbial properties, and requires no preservatives. The composition is non-aqueous and does not dry out, is not tacky or sticky, and does not stain fabric. The composition possesses a low pH to counter the pH elevating effects of semen, soap, menopause and menstruation.

DETAILED DESCRIPTION OF THE INVENTION

In general, the invention is a non-aqueous, lubricating and moisturizing composition directed to, adapted for and suitable for use as a topically or intra-vaginally, particularly during sexual activity, the composition consisting essentially of three primary and essential natural, organic ingredients, to wit, the triglycerides shea butter, coconut oil and grapeseed oil. The composition may contain a scenting component. Triglycerides are a major component of human skin oils, and therefore the combination of shea butter, coconut oil and grapeseed oil possesses excellent compatibility, lubricating and moisturizing characteristics when applied topically or intra-vaginally.

Shea butter is an extract of the African shea tree (*Vitellaria paradoxa*) and is a triglyceride containing stearic acid (20-50%), oleic acid (40-60%), linoleic acid (3-11%), palmitic acid (2-9%), linolenic acid (<1%) and arachidic acid (<1%). Shea butter is safe for topical use and is ingestible. It is a solid at room temperature and melts at body temperature. Shea butter absorbs rapidly into the skin, acts as a refatting agent and binds water. It is also reported to have anti-inflammatory, emollient and humectant properties.

Coconut oil, also known as copra oil, is an edible oil extracted from mature coconuts of the coconut palm (*Cocos nucifera*). It is high in saturated fat and is therefore highly resistant to rancification, being able to last several years without spoiling. It is a triglyceride containing caprylic acid (<9%), decanic acid (<10%), lauric acid (<52%), myristic acid (<19%), palmitic acid (<11%) and oleaic acid (<8%). It is safe for topical use.

Grapeseed oil is a triglyceride extracted from the seeds of grapes. A typical compositional analysis shows (all approximately) linoleic acid (70%), oleic acid (16%), palmitic acid (7%), stearic acid (4%), alpha-linolenic acid (0.1%) and palmitoleic acid (<1%). Grapeseed oil contains approximately 0.8-1.5% unsaponifiables rich in phenols (tocopherols) and steroids (campesterol, beta-sitosterol and stigmasterol), as well as small amounts of vitamin E. Grapeseed oil also contains anti-oxidants.

In the preferred embodiment, the composition consists essentially of approximately 55-70 vol. % shea butter, approximately 25-40 vol. % coconut oil and approximately 1-5 vol. % grapeseed oil. Up to approximately 2 vol. % of a scenting component may be added to the blend, such as for example lavender (*Lavandula*), jasmine (*Jasminum*), sandalwood (*Santulum*), patchouli (*Pogostemon*), sweet orange (*Citrus sinensis*) or ylang-ylang (*Cananga odorata*), alone or in combination.

This composition possesses a pH lower than the natural pH of the human vagina, which is normally 3.5-4.5. A preferred pH value is approximately 3.3. The low pH minimizes bacterial growth, and if the pH rises the vagina becomes susceptible to bacterial and yeast infections. Semen has a pH of 7.2-7.8 and soaps may possess a pH of 9-10, such that either of these may elevate the pH of the vagina. Menopause also results in a naturally higher vaginal pH of 6-7, as does menstruation, which may raise the pH to 7.4. Therefore, the 3.3 pH of the composition helps to maintain a healthy pH level when used as a moisturizer and/or lubricant, the low pH countering the elevated pH values of semen, soap, menopause and menstruation.

The composition requires no added preservatives or added anti-microbial or anti-fungal components, as it is not susceptible to microbial or fungal contamination during manufacture, storage or use. For example, many lubricants contain parabens as a preservative, which has been implicated in breast and/or ovarian cancers. The composition itself possesses anti-microbial and anti-fungal properties, serving to inhibit or eradicate yeasts and molds, in particular, *Staphylococcus aureus, Pseudomonas aeruginosa, E. coli, Salmonella* sp., *Candida albicans* and Bile-tolerant gram negative species (USP <51>, <61> and <62> Criteria; EMSL Analytical), all common pathogens which may result in vaginal infections or other negative conditions. Additional laboratory testing shows the composition is non-cytotoxic (Direct Contact/L929 Mouse Fibroblast; Geneva Laboratories Proc. No. CC1003; Rev. M. Add. ISO Modification; ISO-01 Rev. B); produces no significant signs or symptoms of systemic toxicity (ANSI/AAMI/ISO 10993-11:2006/(R) 2010; Geneva Laboratories Proc. No. CL1026); produces minimal vaginal mucosal irritation (ANSI/AAMI/ISO 10993-10:2010/(R) 2014; Geneva Laboratories Proc. No. CL1021K); and is a dermal non-sensitizer (ANSI/AAMI/ISO 10993-10:2010/(R) 2014; Geneva Laboratories Proc. No. CL1015BB).

The composition has a viscosity of approximately 84,000 centipoise at 24.5° C., an onset melting point of approximately 12° C./54° F. and a complete melting point of approximately 33° C./91° F., and therefore is a high viscosity, soft solid at room temperature that melts at body temperature. This property enables a more controlled application of the composition topically or intra-vaginally in comparison with typical liquid lubricants, which often dry out and/or become sticky, requiring frequent re-application to maintain a suitable level of lubrication. Being non-aqueous, the composition is not hyper-osmolar, as are many water-based lubricants that utilize glycerin, such that there are no deleterious effects from osmotic pressure on the vaginal lining.

The composition may be utilized separately as a topical moisturizer, both externally and intra-vaginally, in addition to its use as a lubricant for sexual intercourse.

The embodiments above are not meant to be limiting, and the true scope and definition of the invention is to be as set forth in the following claims.

I claim:

1. A vaginal lubricating and moisturizing composition consisting essentially of:

approximately 55-70 vol. % shea butter;

approximately 25-40 vol. % coconut oil; and approximately 1-5 vol. % grapeseed oil;

such that said composition possesses a pH of less than approximately 3.5, such that application of said composition within the vagina moisturizes and increases lubrication without raising the natural pH of the vagina.

2. The composition of claim 1, said composition possessing a viscosity of approximately 84,000 centipoise at 24.5° C.

3. The composition of claim 1, said composition being a high viscosity solid at room temperature which melts at body temperature.

4. The composition of claim 1, said composition possessing an onset melting point of approximately 12° C./54° F. and a complete melting point of approximately 33° C./91° F.

5. The composition of claim 1, said composition possessing a viscosity of approximately 84,000 centipoise at 24.5° C., and an onset melting point of approximately 12° C./54° F. and a complete melting point of approximately 33° C./91° F.

6. A non-aqueous, anti-microbial, anti-fungal, vaginal lubricating and moisturizing composition consisting essentially of the combination of:

approximately 55-70 vol. % shea butter;

approximately 25-40 vol. % coconut oil; and approximately 1-5 vol. % grapeseed oil;

wherein the composition possesses a pH of less than approximately 3.5, a viscosity of approximately 84,000 centipoise at 24.5° C., and an onset melting point of approximately 12° C./54° F. and a complete melting point of approximately 33° C./91° F., and wherein application of said composition within the vagina moisturizes and increases lubrication without raising the natural pH of the vagina.

7. The composition of claim 6, said composition being a high viscosity solid at room temperature which melts at body temperature.

8. The composition of claim 1, such that said composition possesses a pH of approximately 3.3.

9. The composition of claim 6, such that said combination results in a pH of approximately 3.3.

10. A vaginal lubricating and moisturizing composition consisting of:

approximately 55-70 vol. % shea butter;

approximately 25-40 vol. % coconut oil; and approximately 1-5 vol. % grapeseed oil;

such that said composition possesses a pH of less than approximately 3.5, such that application of said composition within the vagina moisturizes and increases lubrication without raising the natural pH of the vagina.

11. The composition of claim 10, said composition possessing a viscosity of approximately 84,000 centipoise at 24.5° C.

12. The composition of claim 10, said composition being a high viscosity solid at room temperature which melts at body temperature.

13. The composition of claim 10, said composition possessing an onset melting point of approximately 12° C./54° F. and a complete melting point of approximately 33° C./91° F.

14. The composition of claim 10, said composition possessing a viscosity of approximately 84,000 centipoise at 24.5° C., and an onset melting point of approximately 12° C./54° F. and a complete melting point of approximately 33° C./91° F.

* * * * *